(12) United States Patent
Sinofsky

(10) Patent No.: US 6,547,780 B1
(45) Date of Patent: *Apr. 15, 2003

(54) INFRARED LASER CATHETER SYSTEM

(75) Inventor: Edward Lawrence Sinofsky, Reading, MA (US)

(73) Assignee: CardioFocus, Inc., Norton, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/201,072

(22) Filed: Nov. 30, 1998

Related U.S. Application Data

(63) Continuation of application No. 08/411,581, filed on Mar. 29, 1995, now Pat. No. 5,843,073, which is a continuation of application No. 08/049,147, filed on Apr. 19, 1993, now abandoned, which is a division of application No. 07/568,348, filed on Aug. 15, 1990, which is a continuation of application No. 07/257,760, filed on Oct. 14, 1988, now Pat. No. 4,950,266, which is a continuation of application No. 07/014,990, filed on Feb. 17, 1987, now abandoned, which is a continuation of application No. 06/761,188, filed on Jul. 31, 1985, now abandoned.

(51) Int. Cl.$^7$ .............................................. A61B 18/28
(52) U.S. Cl. .................................. 606/10; 606/3; 606/7; 606/13
(58) Field of Search .................................. 606/3, 7, 10–17

(56) References Cited

U.S. PATENT DOCUMENTS

| | | | |
|---|---|---|---|
| 1,751,584 A | 3/1930 | Hansell | |
| 3,327,712 A | 6/1967 | Kaufman | |
| 3,533,707 A | 10/1970 | Weiss | |
| 3,769,963 A | 11/1973 | Goldman et al. | |
| 3,858,577 A | 1/1975 | Bass et al. | |

(List continued on next page.)

FOREIGN PATENT DOCUMENTS

| EP | 0144764 | 6/1985 |
|---|---|---|
| EP | 0152766 | 8/1985 |

(List continued on next page.)

OTHER PUBLICATIONS

Abela, G. et al., "Effects of Carbon Dioxide, Nd–YAG, and Argon Laser Radiation on Coronary Atheromatous Plaques," *The American Journal of Cardiology*, vol. 50, No. 6, 1199–1205 (Dec. 1982).

(List continued on next page.)

*Primary Examiner*—David M. Shay
(74) *Attorney, Agent, or Firm*—Thomas J. Engellenner; Nutter McClennen & Fish LLP

(57) ABSTRACT

Laser energy produced by a laser operating In the mid-infrared region (approximately 2 micrometers) Is delivered by an optical fiber in a catheter to a surgical site for biological tissue removal and repair. Disclosed laser sources which have an output wavelength in this region include: Holmium-doped Yttrium Aluminum Garnet (Ho:YAG), Holmium-doped Yttrium Lithium Fluoride (Ho:YLF), Erbium-doped YAG, Erbium-doped YLF and Thulium-doped YAG. For tissue removal, the lasers are operated with relatively long pulses at energy levels of approximately 1 joule per pulse. For tissue repair, the lasers are operated in a continuous wave mode at low power. Laser output energy is applied to a silica-based optical fiber which has been specially purified to reduce the hydroxyl-ion concentration to a low level. The catheter may be comprised of a single optical fiber or a plurality of optical fibers arranged to give overlapping output patterns for large area coverage.

14 Claims, 6 Drawing Sheets

U.S. PATENT DOCUMENTS

| | | |
|---|---|---|
| 3,865,113 A | 2/1975 | Sharon et al. |
| 3,884,236 A | 5/1975 | Krasnov |
| 3,947,780 A | 3/1976 | Rice et al. |
| 3,982,541 A | 9/1976 | L'Esperance |
| 3,983,511 A | 9/1976 | Fricke |
| 4,110,702 A | 8/1978 | Chicklis |
| 4,141,362 A | 2/1979 | Wurster |
| 4,146,019 A | 3/1979 | Bass et al. |
| 4,170,997 A | 10/1979 | Pinnow et al. |
| 4,207,874 A | 6/1980 | Choy |
| 4,233,493 A | 11/1980 | Nath |
| 4,266,548 A | 5/1981 | Davi |
| 4,309,998 A | 1/1982 | Aron nee Rosa et al. |
| 4,321,559 A | 3/1982 | Esterowitz et al. |
| 4,330,763 A | 5/1982 | Esterowitz et al. |
| 4,350,150 A | 9/1982 | Kubota et al. |
| 4,355,893 A | 10/1982 | Chicklis |
| 4,383,729 A | 5/1983 | Suzuki et al. |
| 4,386,428 A | 5/1983 | Baer |
| 4,402,311 A | 9/1983 | Hattori |
| 4,418,688 A | 12/1983 | Loeb |
| 4,425,503 A | 1/1984 | Watkins et al. |
| 4,445,918 A | 5/1984 | Modone et al. |
| 4,448,188 A | 5/1984 | Loeb |
| 4,454,882 A | 6/1984 | Takano |
| 4,458,683 A | 7/1984 | Saito et al. |
| 4,469,098 A | 9/1984 | Davi |
| 4,470,407 A | 9/1984 | Hussein |
| 4,503,854 A | 3/1985 | Jako |
| 4,504,297 A | 3/1985 | Kosinski et al. |
| 4,515,612 A | 5/1985 | Burrus, Jr. et al. |
| 4,519,390 A | 5/1985 | Horne |
| 4,538,608 A | 9/1985 | L'Esperance, Jr. et al. |
| 4,556,057 A | 12/1985 | Hiruma et al. |
| 4,559,942 A | 12/1985 | Eisenberg |
| 4,566,453 A | 1/1986 | Kumano et al. |
| 4,566,765 A | 1/1986 | Miyauchi et al. |
| 4,572,189 A | 2/1986 | Smith et al. |
| 4,576,177 A | 3/1986 | Webster, Jr. |
| 4,587,972 A | 5/1986 | Morantte, Jr. |
| 4,592,353 A | 6/1986 | Daikuzono |
| 4,633,866 A * | 1/1987 | Peyman et al. ............... 606/4 |
| 4,641,650 A | 2/1987 | Mok |
| 4,641,912 A | 2/1987 | Goldenberg |
| 4,648,892 A | 3/1987 | Kittrell et al. |
| 4,654,024 A | 3/1987 | Crittendon et al. |
| 4,669,467 A | 6/1987 | Willett et al. |
| 4,672,969 A * | 6/1987 | Dew ............................ 606/11 |
| 4,681,104 A | 7/1987 | Edelman |
| 4,685,458 A | 8/1987 | Leckrone |
| 4,686,979 A | 8/1987 | Gruen et al. |
| 4,718,417 A | 1/1988 | Kittrell et al. |
| 4,732,448 A | 3/1988 | Goldenberg |
| 4,750,486 A | 6/1988 | Butler et al. |
| 4,765,330 A | 8/1988 | Bach |
| 4,775,361 A | 10/1988 | Jacques et al. |
| 4,784,132 A | 11/1988 | Fox et al. |
| 4,784,135 A | 11/1988 | Blum et al. |
| 4,799,754 A | 1/1989 | Goldenberg |
| 4,800,876 A | 1/1989 | Fox et al. |
| 4,817,601 A | 4/1989 | Roth et al. |
| 4,819,632 A | 4/1989 | Davies |
| 4,822,136 A * | 4/1989 | Hicks, Jr. ................... 350/142 |
| 4,830,460 A | 5/1989 | Goldenberg |
| 4,848,336 A | 7/1989 | Fox et al. |
| 4,848,339 A | 7/1989 | Rink et al. |
| 4,850,351 A | 7/1989 | Herman et al. |
| 4,852,567 A | 8/1989 | Sinofsky |
| 4,854,315 A | 8/1989 | Stack et al. |
| 4,860,743 A | 8/1989 | Abela |
| 4,862,886 A | 9/1989 | Clarke et al. |
| 4,878,492 A | 11/1989 | Sinofsky et al. |
| 4,905,689 A | 3/1990 | Stack et al. |
| 4,913,142 A | 4/1990 | Kittrell et al. |
| 4,917,084 A | 4/1990 | Sinofsky |
| 4,929,246 A | 5/1990 | Sinofsky |
| 4,950,266 A | 8/1990 | Sinofsky |
| 4,967,745 A | 11/1990 | Hayes et al. |
| 4,994,059 A | 2/1991 | Kosa et al. |
| 4,994,060 A | 2/1991 | Rink et al. |
| 5,037,421 A | 8/1991 | Boutacoff et al. |
| 5,147,354 A | 9/1992 | Boutacoff et al. |
| 5,196,004 A | 3/1993 | Sinofsky |
| 6,159,203 A * | 12/2000 | Sinofsky ........................ 606/7 |

FOREIGN PATENT DOCUMENTS

| | | |
|---|---|---|
| EP | 0153847 | 9/1985 |
| EP | 0178464 | 4/1986 |
| EP | 0214712 | 3/1989 |
| GB | 2017506 | 10/1979 |
| GB | 2125986 | 3/1984 |
| SU | 1073914 | 6/1985 |
| WO | 8301311 | 4/1983 |
| WO | 8301893 | 6/1983 |
| WO | 8404879 | 12/1984 |
| WO | 8606642 | 11/1986 |

OTHER PUBLICATIONS

Anderson, R. and Parrish, J., "Microvasculature Can be Selectively Damaged Using Dye Lasers: A Basic Theory and Experimental Evidence in Human Skin," *Lasers in Surgery and Medicine*, vol. 1, 263–76 (1981).

Anderson, R. and Parrish, J., "Selective Photothermolysis: Precise Microsurgery by Selective Absorption of Pulsed Radiation," *Science*, vol. 220, 524–7 (Apr. 29, 1983).

Beckman et al., "Limbectomies, Keratectomies, and Keratostomies Performed with a Rapid–Published Carbon Dioxide Laser," *Am. J. Ophthal.*, vol. 71, No. 6, 1277–83 (Jun. 1971).

Deckelbaum, L., et al., "Reduction of Laser–Induced Pathologic Tissue Injury Using Pulsed Energy Delivery," *Am. J. Cardiol.*, vol. 56, No. 10, 662–7 (Oct. 1, 1985).

Esterowitz, L., "Angioplasty with a Laser and Fiber Optics at 2.9 um," *Spie Conference*, Los Angeles, CA, (Jan. 1986).

Fraser, A.B. et al., "Pulsed Laser Iridotomy Apparatus," The Johns Hopkins University—*Applied Physics Laboratory*, (Oct. 1977–Sep. 1978).

Fugii, H. et al., "Fibre Bundle Scanner for Laser Photocoagulation Treatment," *Optics & Laser Technology*, 39–40 (Feb. 1982).

Goldman, L. et al., The Biomedical Laser: Technology and Clinical Applications, (1981).

Horn et al., "A New "Cool" Lens Capsulotomy Laser," *Am. Intraocular Implant Society Journal*, vol. 8, 337–42 (Fall 1982).

Isner, J. et al., "Mechanism of Laser Ablation in an Absorbing Fluid Field," *Lasers in Surgery and Medicine*, vol. 8, No. 6, 543–54 (1988).

Kay, D., "The Happy Merger of Fiber Optics and Lasers," Information Retrieval No. 22, News RT 167 *Electronic Design*, vol. 17, (Jun. 21, 1969).

Koechner, W., "Solid State Laser Engineering," Springer–Verlag, New York Heidelberg Berlin (1976).

Lee, G. et al., "Current and Potential Uses of Lasers in the Treatment of Atherosclerotic Disease," *Chest*, vol. 85, No. 3, 429–34 (Mar. 1984).

Lee, G. et al., "Limitations, Risks and Complications of Laser Recanalization: A Cautious Approach Warranted," *The American Journal of Cardiology*, vol. 56, 181–5 (Jun. 1, 1985).

McGuff, P. et al., "Studies of the Surgical Applications of Laser Light (Light Amplification by Stimulated Emission of Radiation)," *Surgical Form*, American College of Surgeons, Chicago, vol. 14 (1963).

Motamedi, M. et al., "Interaction of Laser Radiation with Plaque and Vessel Wall," *ICALEO*, (1984).

Sa'ar, A. et al., "Transmission of Pulsed Laser Beams Through "Opaque" Liquids by a Cavitation Effect," Appl. Phys. Lett., vol. 50, No. 22, 1556–8 (1987).

Sinofsky, E., "Calculated Temperature Distribution in Cylindrical Tissue Volume Under Laser Irradiation Below the Vaporization Threshold," *Lasers in Medicine*, Proceedings of SPIE, vol. 712, 78 (1987).

Sinofsky, E., "Comparative Thermal Modeling of Er:YAG, Ho:YAG and CO2 Laser Pulses for Tissue Vaporization, Proceedings for SPIE," *The International Society for Optical Engineering, Lasers in Medicine*, vol. 712, 188–92 (1986).

Sinofsky, E. et al., "Measurement of Argon Laserbeam Spreading Through Arterial Plaque," *Lasers in the Life Sciences*, vol. 1, No. 2, 143–50 (1986).

Van Leewen, "Noncontact Tissue Ablation by Holmium: YSGG Laser Pulses in Blood," *Lasers Surgery Medical*, vol. 2, No. 1, 26–34 (1991).

Ward, H., "Laser Recannalization of Atheromatous Vessels Using Fiber Optics," *Lasers in Surgery and Medicine*, vol. 4, 353–63 (1984).

Wolbarsht, M., "Interactions Between Material Processing and Surgery," *ICALEO*, 4/L.I.A., vol. 32 (1982).

* cited by examiner

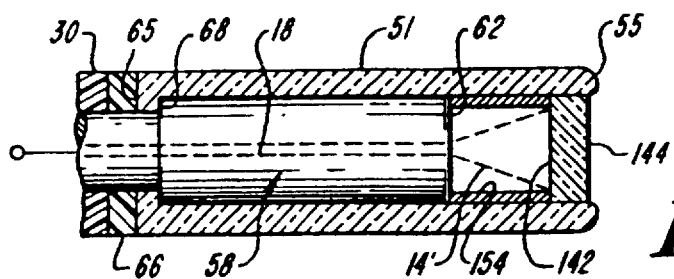
*FIG. 6*
*FIG. 7*
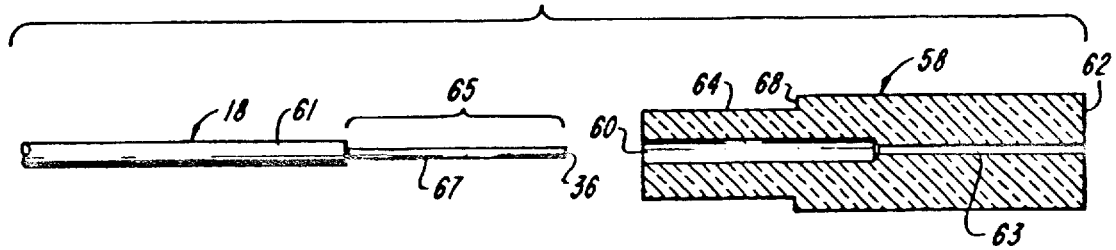
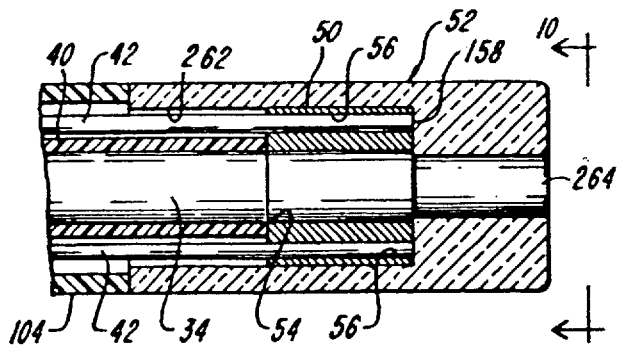
*FIG. 9*
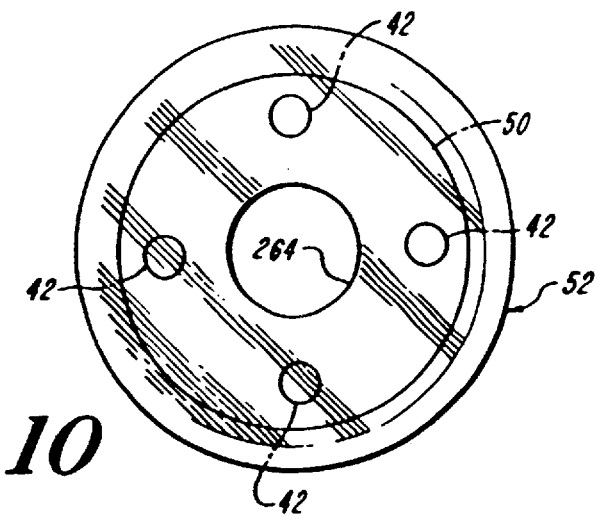
*FIG. 10*

INFRARED LASER CATHETER SYSTEM

This application is a continuation of application Ser. No. 08/411,581, filed Mar. 29, 1995, U.S. Pat. No. 5,843,073 which is a continuation of Ser. No. 08/049,147, filed Apr. 19, 1993 now abandoned, which is a divisional of Ser. No. 07/568,348, filed Aug. 15, 1990, which is a continuation of Ser. No. 07/257,760, filed Oct. 14, 1988, U.S. Pat No. 4,450,266 which is a continuation of Ser. No. 07/014,990, filed Feb. 17, 1987 now abandoned, which is a continuation Ser. No. 06/761,188, filed Jul. 31, 1995 now abandoned. The contents of all of the aforementioned application(s) are hereby incorporated by reference.

FIELD OF THE INVENTION

This invention relates to laser catheters and optical fiber systems for generating and transmitting energy to a surgical site in a living body for the purposes of tissue removal or repair.

BACKGROUND OF THE INVENTION

While lasers have been used for many years for industrial purposes such as drilling and cutting materials, it is only recently that surgeons have begin to use lasers for surgical operations on living tissue. To this end, laser energy has been used to repair retinal tissue and to cauterize blood vessels in the stomach and colon.

In many surgical situations, it is desirable to transmit laser energy down an optical fiber to the surgical location. if this can be done, the optical fiber can be included in a catheter which can be inserted into the body through a small opening, thus reducing the surgical trauma associated with the operation. In addition, the catheter can often be maneuvered to surgical sites which are so restricted that conventional scalpel surgery is difficult, if not impossible. For example, laser energy can be used to remove atherosclerotic plaque from the walls of the vasculature and to repair defects in small-diameter artery walls.

A problem has been encountered with laser surgery in that prior art lasers which have been used for industrial purposes often have characteristics which are not well suited to percutaneous laser surgery. For example, a laser which in conventionally used for scientific purposes is an excimer laser which Is a gas laser that operates with a gas mixture such as Argon-Fluorine, Krypton-Fluorine or Xenon-Fluorine. Another common industrial laser is the carbon dioxide or $CO_2$ laser.

Both the excimer laser and the $CO_2$ laser have been used for surgical purposes with varying results. One problem with excimer lasers is that they produce output energy having a wavelength in the range 0.2–0.5 micrometers. Blood hemoglobin and proteins have a relatively high absorption of energy in this wavelength range and, thus, the output beam of an excimer laser has a very short absorption length in these materials (the absorption length is the distance in the materials over which the laser beam can travel before most of the energy is absorbed). Consequently, the surgical site in which these lasers are to be used must be cleared of blood prior to the operation, otherwise most of the laser energy will be absorbed by intervening blood before it reaches the surgical area. While the removal of blood is possible if surgery is performed on an open area it is often difficult if surgery is to be performed via a catheter located in an artery or vein.

An additional problem with excimer lasers is that the output energy pulse developed by the laser is very short, typically about ten nanoseconds. In order to develop reasonable average power, pulses with extremely high peak power must be used. When an attempt is made to channel such a high peak power output into an optical fiber, the high peak power destroys the fiber. Thus, excimer lasers have a practical power limit which is relatively low. Consequently, when these lasers are used for biological tissue removal, the operation is slow and time consuming.

The $CO_2$ laser has other drawbacks. This laser generates output energy with a wavelength on the order of 10 micrometers. At this wavelength, the absorption of blood hemoglobin is negligible but the absorption by water and tissue is relatively high. Scattering at this wavelength is also very low. Although the $CO_2$ laser possesses favorable characteristics for surgical applications in that it has low scattering and high absorption in tissue, it suffers from the same drawback as excimer lasers in that the absorption length is relatively short due to the high absorption of the laser energy in water. Thus, the surgical area must be cleared of blood prior to the operation.

Unfortunately, the $CO_2$ laser also suffers from a serious additional problem. Due to the long wavelength, the output energy from the carbon dioxide laser cannot be presently transmitted down any optical fibers which are suitable for use in percutaneous surgery (present fibers which can transmit energy from a $CO_2$ laser are either composed of toxic materials, are soluble in water or are not readily bendable, or possess a combination of the previous problems) and, thus, the laser is only suitable for operations in which the laser energy can be either applied directly to the surgical area or applied by means of an optical system comprised of prisms or mirrors.

Accordingly, it is an object of the present invention to provide a laser catheter system which uses laser energy of a wavelength that is strongly absorbed in water, in bodily tissues and atherosclerotic plaque.

It is another object of the present invention to provide a laser catheter system which is capable of providing laser energy that can be transmitted through existing silica-based optical fibers.

It is a further object of the present invention to provide a laser catheter system in which optical scattering is minimized and which has a medium-length absorption length to confine the energy to the area of interest.

It is yet another object of the present invention to provide an optical catheter system with a laser that can be operated on either a pulsed mode or a continuous wave mode.

It is still another object of the present invention to provide a laser catheter system which can be used for biological material removal and biological material repair.

SUMMARY OF THE INVENTION

The foregoing objects are achieved and the foregoing problems are solved in one illustrative embodiment of the invention in which a laser catheter system employs a laser source operating in the wavelength region of 1.4–2.2 micrometers. Illustrative laser sources operating this region are Holmium-doped YAG, Holmium-doped YLF, Erbium-doped YAG, Erbium-doped YLF and Thulium-doped YAG lasers.

In the inventive laser system, the above-noted lasers are used with a specially-treated silica fiber that has been purified to reduce the concentration of hydroxyl (OH—) ions.

For biological tissue removal, the laser source may be operated in a pulsed mode with a relatively long pulse of approximately 0.2–5 milliseconds at an energy level of approximately 1–2 joules per pulse. With this time duration and energy level, the peak power of the laser pulse is approximately 1 kilowatt. This amount of power can easily be tolerated by the silica fiber, but is sufficient for rapid material removal. With a repetition rate in the range of 1–10 hertz, the average power delivered to a surgical site by such a laser will be under 10 watts.

Alternatively, for biological tissue repair, the laser source can be operated in a low power continuous wave mode to repair, by coagulation, of tissue by a process similar to "spot welding".

BRIEF DESCRIPTION OF THE DRAWING

FIG. 6 of the drawing is an enlarged cross-section of the probe tip the single fiber catheter shown in FIG. 5.

FIG. 7 is a schematic diagram of a wire-guided catheter which employs four optical fibers to increase the area which can be irradiated with the laser light.

FIG. 9 of the drawing is a schematic diagram of the beam pattern produced by the four-fiber catheter at the surgical location.

FIG. 10 is an end view of the probe tip of the catheter in the direction 10–10 of FIG. 9.

DETAILED DESCRIPTION OF THE PREFERRED EMBODIMENT

Figure 1:
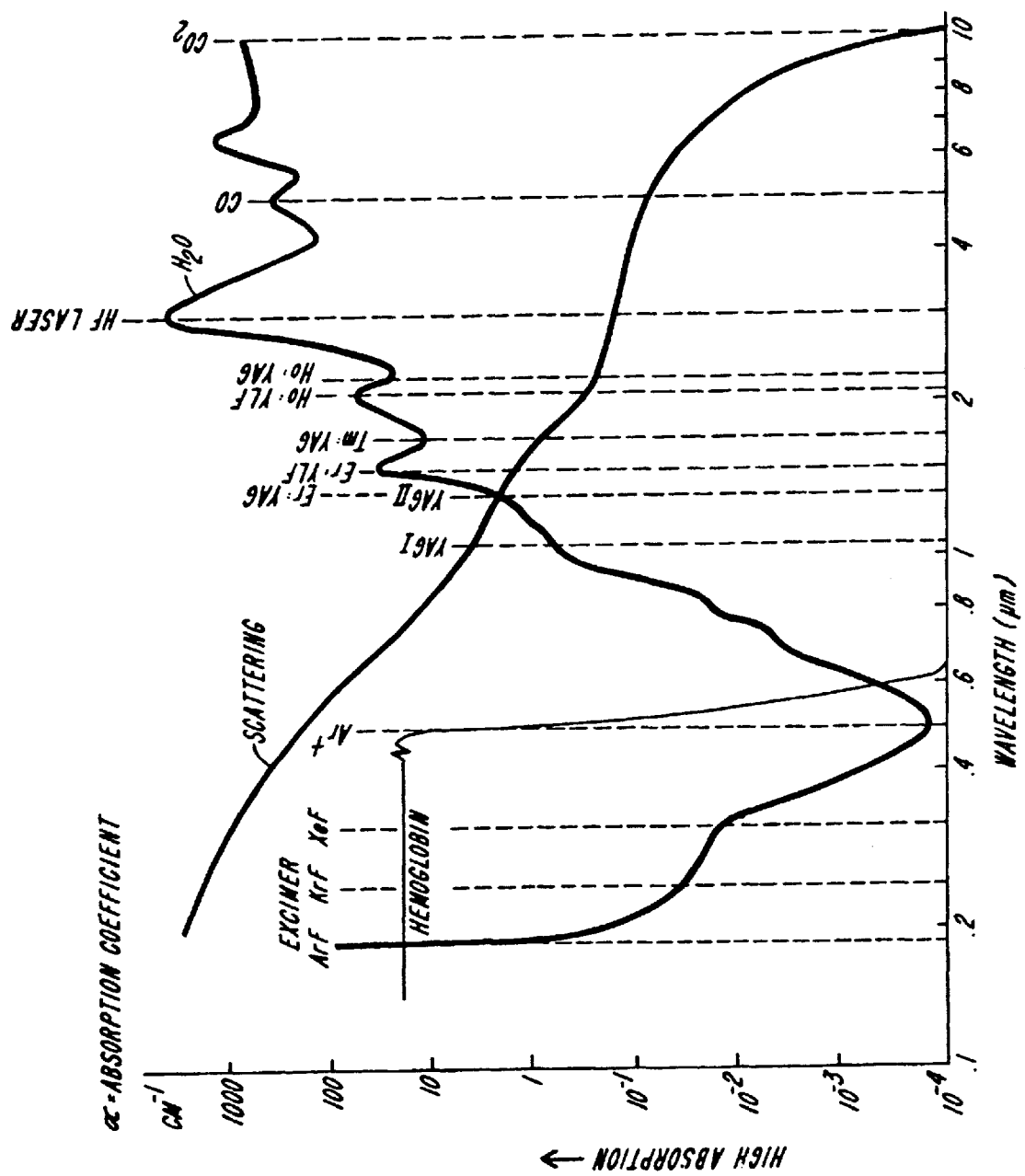
FIG. 1 shows a sketch of absorption of electromagnetic energy versus wavelength and electromagnetic energy scattering versus wavelength.

The absorption and scattering characteristics versus output wavelength of a plurality of known laser systems are shown in FIG. 1. FIG. 1 has a logarithmic scale representing the absorption coefficient in units of $cm^{-1}$ along the vertical axis and the incident energy wavelength in micrometers along the horizontal axis.

From FIG. 1, it can be seen that excimer laser systems which utilize conventional gas mixtures such as Argon-Fluorine, Krypton-Fluorine and Xenon-Fluorine, and Argon gas lasers produce output energy which falls in the 0.2–0.5 micrometer wavelength region. In this region, the absorption of blood hemoglobin and proteins is very high. Consequently, the absorption length is very short (about 5–10 microns) and virtually no blood can be present between the fiber end and the surgical site during the operation. Thus, it is necessary to remove blood from the surgical area when these lasers are used for surgical purposes.

In addition, for lasers such as Argon, the absorption of water reaches a minimum at 0.5 micrometers so that it is necessary to use a higher power laser than is desirable to achieve sufficient power in the surgical area for material cutting and removal. Also, due to the low absorption of the laser output in water and hemoglobin, the absorption length is very long (approximately 1 mm). In addition, scattering for these lasers is relatively high, causing difficulty in controlling the laser energy and a danger of tissue damage outside the surgical area due to scattering of the laser energy.

At the other end of the wavelength spectrum shown in FIG. 1 are carbon monoxide and carbon dioxide lasers producing outputs at 5 and 10 micrometers, respectively. At these wavelengths scattering is negligible and absorption by water and tissue is relatively high and thus both lasers have good surgical properties. Unfortunately, due to the high absorption of water, the absorption length is relatively short (about 20 microns). Further, silica-based optical fibers in present use which are suitable for percutaneous surgical use have a practical "cutoff" in transmission which occurs approximately at 2.3 micrometers, and, thus, the output energy from carbon monoxide and carbon dioxide lasers cannot be transmitted through such an optical fiber.

Figure 2:
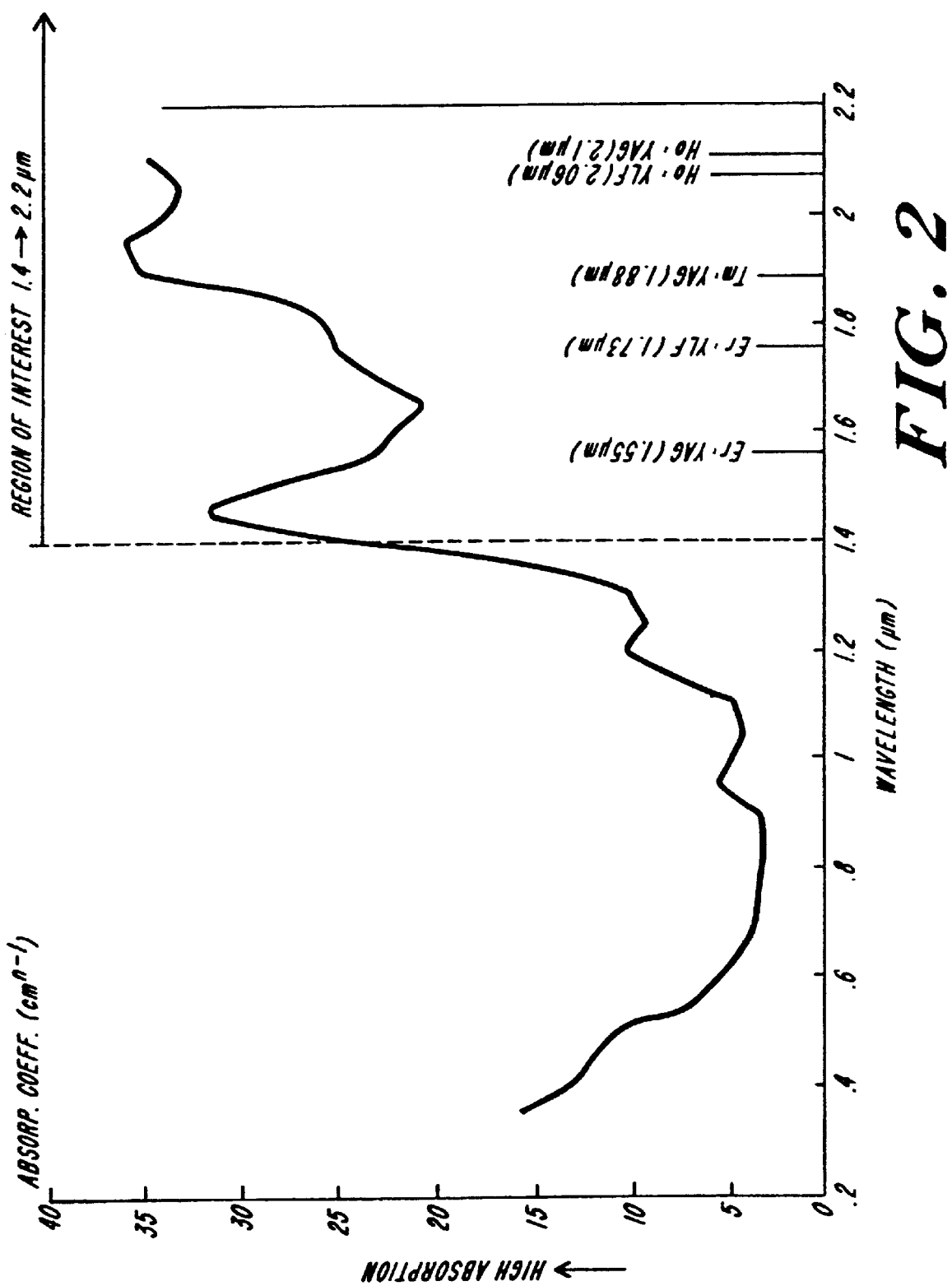
FIG. 2 shows an absorption versus wavelength plot for atherosclerotic plaque obtained in a carotid endarterectomy with the region of interest for the inventive laser sources (1.4–2.2 micrometers) outlined.

In accordance with the invention, laser sources of interest are those that lie in the wavelength range of approximately 1.4–2.15 micrometers. As shown in FIG. 1, in this range, the energy absorption of water is relatively high whereas optical scattering is relatively low. Illustrative lasers which are useful with the present invention comprise Erbium-doped Yttrium Aluminum Garnet (YAG) with a wavelength of 1.55 micrometers, Erbium-doped Yttrium Lithium Fluoride (YLF) with a wavelength of 1.73 micrometers, Thulium-doped YAG with a wavelength of 1.88 micrometers, Holmium YLF with a wavelength of 2.06 micrometers and Holmium YAG at a wavelength of 2.1 micrometers. The absorption of the laser energy produced by lasers in this latter group by water is moderately high and, consequently, the absorption by biological tissues of such energy will also be relatively high. However, the absorption by water is not as high as the absorption of CO and $CO_2$ laser energy. Thus, the absorption length will be longer for the lasers operating in the 1.4–2.2 micron range. Typically, the absorption length In the body for these latter lasers is about 200 microns. Therefore, it is still possible to operate satisfactorily even with 10–30 microns of blood between the fiber end and the surgical site. of particular interest is the absorption of the laser energy by atherosclerotic plaque, since an important use of laser catheter systems is angioplasty, particularly the clearing of blocked arteries. FIG. 2 is a plot of the absorption by plaque of electromagnetic energy versus wavelength for energy in the wavelength range of 0.2–2.2 micrometers. As shown in FIG. 2, the absorption by plaque of electromagnetic energy reaches a minimum in the 0.8–1 micrometer wavelength range and generally increases with increasing wavelength in the wavelength region of 1–2.2 micrometers.

In the wavelength range from 1.4–2.2 micrometers, the wavelength range produced by laser in the above-mentioned group, the absorption by plaque is at a relatively high value.

Figure 3:
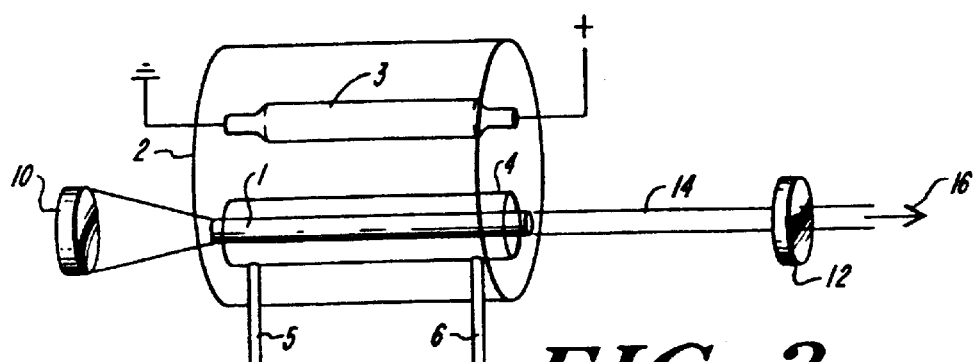
FIG. 3 of the drawing is a schematic diagram of a typical solid state laser construction used in the inventive laser sources.

A schematic diagram of a typical solid-state laser construction is shown in FIG. 3. The laser assembly consists of a laser crystal 1 and an excitation device such as a flashlamp 3. Typically, for the crystal compositions disclosed above, the laser crystal must be cooled to cryogenic temperature to provide low laser-threshhold operation. Cryogenic cooling is typically provided by enclosing crystal 1 in a quartz or fused-silica jacket 4 through which liquid nitrogen is circulated. Liquid nitrogen enters jacket 4 by means of an inlet pipe 5 and leaves by means of an outlet pipe 6. The laser cavity is formed by a high-reflectivity concave mirror 10 and a partial reflector 12.

Generally, the crystal is excited by optical pumping which is, in turn, accomplished by irradiating the crystal with light from a flashlamp 3. A flashlamp which is typically used with the inventive laser compositions is a high-pressure Xenon flashlamp. Lamp 3 may also be surrounded by a quartz flow tube (not shown) through which coolant is pumped.

Crystal 1 and flashlamp 3 are enclosed in a reflector 2 which concentrates the flashlamp energy into the laser crystal. To maximize energy transfer from lamp 3 to crystal 1, the inner surface of reflector 2 is coated with a material chosen to have high-reflectivity at the pumping wavelength of the laser crystal—illustratively, aluminum or silver, In order to provide thermal insulation to prevent condensation on the system optics, it may be necessary to evacuate the interior of reflector 2 or to provide a vacuum jacket around crystal 1.

The construction of cryogenic solid-state lasers is conventional and described in a variety of sources; accordingly such construction will not be discussed further in detail herein. A more complete discussion of construction details of a typical cryogenic laser is set forth in an article entitled "TEM$_{oo}$ Mode Ho:YLF laser", N. P. Barnes, D. J. Gettemy, N. J. Levinos and J. E. Griggs, *Society of Photo-Optical Instrumentation Engineers*, Volume 190—LASL Conference on Optics 1979, pp 297–304.

Figure 4:
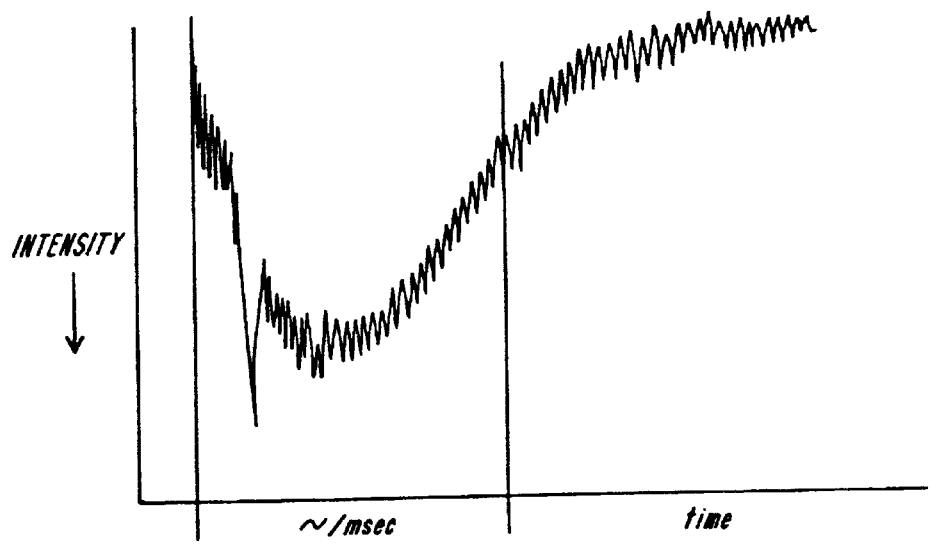
FIG. 4 of the drawing is a plot of laser output intensity versus time for a typical pulse shape developed by a laser shown in FIG. 3 when used for tissue removal.

FIG. 4 of the drawing is a plot of the illustrative pulse shape developed by a laser in the preferred group when used in the "material removal" mode. FIG. 4 shows light intensity along the vertical axis increasing in the downward direction versus time increasing towards the right. Although, as shown in FIG. 4, the laser source has been adjusted to produce an output pulse of relatively long time duration, most of the output energy is released within approximately 1 millisecond of the beginning of the pulse. It should also be noted, as illustrated in FIG. 4, that lasers in the preferred laser group exhibit a "spiking" phenomenon caused by internal relaxation-oscillations in the laser crystal. The spiking behavior causes local increases in laser intensity which have a large magnitude, but a very short time duration. Similar "spiking" behavior has been found advantageous when lasers are used to drill metals and other materials for industrial purposes and it is believed that such "spiking" behavior enhances the laser usefulness for biological material removal.

Figure 5:
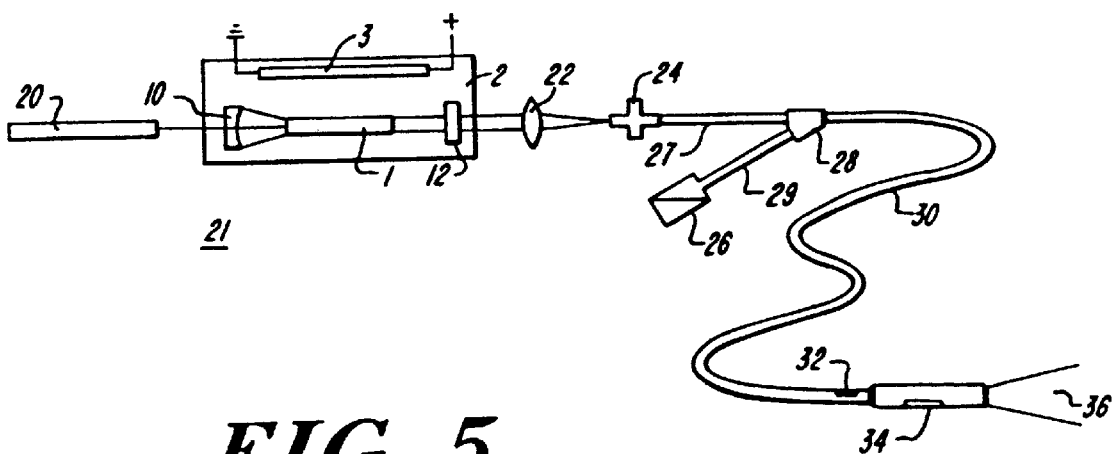
FIG. 5 is a schematic diagram of a laser catheter which employs a single optical fiber for transmitting laser energy to a surgical location.

FIG. 5 is a schematic diagram of a laser/catheter system employing a solid state laser of the type shown in detail in FIG. 3. More specifically, the infrared output energy of laser 21 is focused by a conventional focusing lens onto the end of the optical fiber which is held in a conventional fiber optic connector 24. Fiber optic connector 24 is, in turn, connected to a tube 27 which houses a single optical fiber. Tube 27 is connected to a conventional two-lumen catheter 30 by means of a bifurcation fitting 28.

Illustratively, catheter 30 has two lumens passing axially therethrough to its distal end 34 so that an optical fiber can pass through one lumen and transmit laser energy from fiber optic connector 24 to lens tip 34. As previously mentioned, the optical fiber which passes through the catheter is specially purified to reduce the hydroxyl ion concentration to a low level, thus preventing the laser energy which is transmitted down the fiber from being highly absorbed in the fiber material. A fiber which is suitable for use with the illustrative embodiment is a fused-silica optical fiber part no. 822W manufactured by the Spectran Corporation located in Sturbridge, Mass.

Advantageously, the mirrors and lenses (10, 12 and 22) which are used to form the IR laser cavity and focus the output energy beam are generally only reflective to energy with a wavelength falling within a narrow wavelength band and transparent to energy at other wavelengths. Consequently, the mirrors and lenses are transparent to visible light. An aiming laser 20 (for example, a conventional helium-neon laser) which generates visible light may be placed in series with IR laser 21 to generate a visible light beam. This light beam may be used to align mirrors 10 and 12 and to adjust focussing lens 22 so that the optical fiber system can be aligned prior to performing surgery.

Also, the optical fibers used to transmit the IR energy from laser 21 to the surgical area can also be used to transmit the visible light from the aiming laser 20 to the surgical area. Thus, when the inventive system is used in performing surgery where the surgical area is visible to the surgeon, the light produced by laser 20 passes through the optical fiber in catheter 30 and can be used to aim the probe tip before laser 21 is turned on to perform the actual operation.

The second lumen in catheter 30 is provided for transmission of a flushing fluid or to apply auction to the probe lens tip area to clear the area of blood during surgery. This latter lumen is connected through bifurcation fitting 28 to a second tube 29. Tube 29 may illustratively be terminated by a standard Luer-Lok fitting 26 which allows connection of the catheter to injectors and standard flow fittings. Solutions injected into the catheter through tube 29 pass through the lumen in catheter 30 and exit at the distal end via a small orifice 32.

Probe tip 34 consists of a lens arrangement which forms the laser energy into a beam 36 which is used to perform the surgical operations. An enlarged view of the probe tip in shown in FIGS. 6 and 7.

To ensure that the distal end of optical fiber 18 is spaced and oriented in a precise position with respect to the end of the probe, fiber 18 is mounted in a high-precision holder 58 which has a reduced diameter end 64 that forms a shoulder 68. Shoulder 68, as will hereinafter be described, is used to bold the probe tip assembly together. Bolder 38 has a precision-formed axial bore made up of two sections, including a large-diameter section 60 and a narrow-diameter section 63. Bolder 58 may be made of glass, ceramic or other material capable of being formed to specified dimensions with precise tolerances.

In order to attach holder 58 to the end of fiber 18, the fiber to first prepared as shown in FIG. 7. More particularly, prior to insertion of fiber 18 into holder 58, a portion of buffer sheath 61 is removed, exposing a length of optically-conductive core 65. Care is taken when stripping buffer sheath 61 from the fiber not to damage the layer of reflective cladding 67 located on the surface of core 65. After stripping, fiber 18 is inserted into holder 58 so that core 65 extends into the small-diameter bore 63 and sheath 61 extends into the large-diameter bore 60. After fiber 18 has been inserted into holder 58, it may be fastened by epoxy cement to permanently affix the components. To complete the assembly, the end of fiber 18 which protrudes beyond surface 62 of holder 58 may be finished flush with the surface by grinding the assembly or by carefully cleaving the fiber.

Referring to FIG. 6, holder 58 (with fiber 18 fastened inside) is mounted within a glass tube 51 to shield the assembly. The front surface, 62, of holder 58 is spaced from the inner surface 142 of planar lens 144, which may be comprised of glass or sapphire, by means of a spacing ring 154. Ring 154 may illustratively be made of radiopaque material so that the catheter tip can be located inside the patient by means of a fluoroscope.

Glass tubing 51 is bent over shoulder 68 of holder 58 to form a constricted end, 65, which holds the probe tip assembly together. A fillers 66, which may be made of a plastic such as TEFLON (trademark of the DuPont corporation for polytetrafluoroethylene) fills the annular space between catheter, body 30 and end 65 of glass tube 51. The outer diameter of the entire assembly from catheter body 30 to glass tube 51 is substantially the same, providing a smooth, uniform surface along the entire length of the catheter as indicated in FIG. 6.

Figure 8:
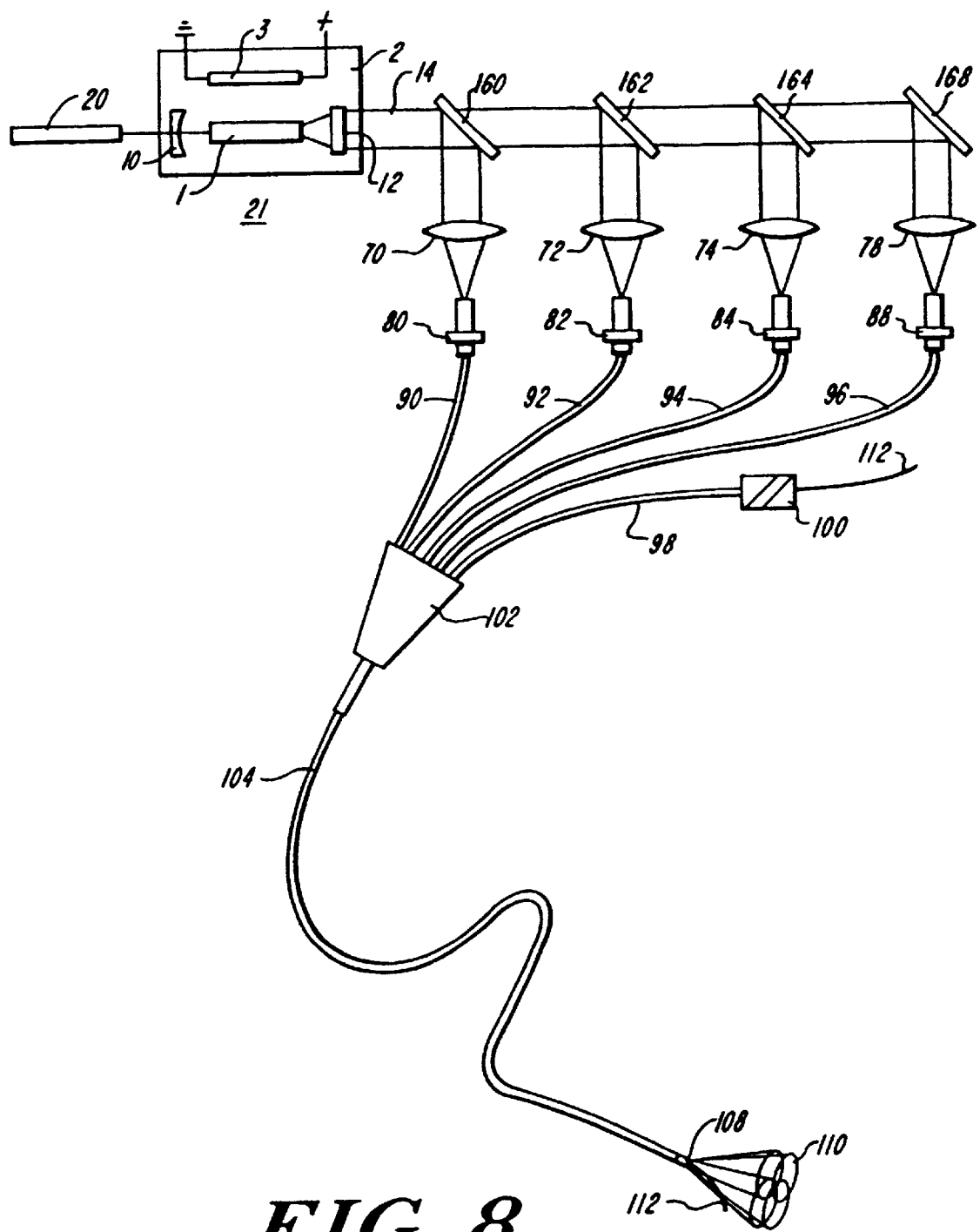
FIG. 8 of the drawing is an enlarged cross-sectional view of the probe tip of the catheter shown in FIG. 7 showing the four optical fibers.

FIG. 8 shows a schematic diagram of a wire-guided, four-fiber catheter for use with the present invention. The laser system is set up as previously described with the infrared laser 21 constructed in accordance with the above disclosure. A visible helium-neon aiming laser 20 may also be used in line with laser 21 for aiming purposes as discussed with the single fiber catheter. The output of the infrared laser 21 is directed towards a set of four mirrors 60–68 arranged at a 45° angle with respect to the axis of beam 14.

The first mirror, 60, has a 25% reflective surface and directs approximately ¼ of the energy to focusing lens 70. The second mirror of the set, 62, is a 33% reflector which directs ¼ of the total energy to focusing lens 72. Mirror 64 is a 50% reflector which directs ¼ of the total laser output to focusing lens 74. The last mirror in the set, mirror 68, is a 100% reflector which directs the remaining ¼ of the total energy to focusing lens 78. Mirrors 60–68 and lenses 70–78 are conventional devices. Focusing lenses 70–78 focus the output energy from IR laser 21 onto four fiber optic connectors, 80–88. Connectors 80–88 are connected, respectively, to tubes 90–96 which are all connected, via a branch connector 102, to catheter 104. Each of tubes 90–96 contains a single optical fiber which transmits ¼ of the total laser output energy through the catheter body to the catheter tip 108. An additional tube 98 is provided which is connected to branch fitting 102 and to a conventional Luer-Lok connector, 100. This latter tube is connected to a central lumen in catheter body 104 through which flushing solutions may be injected or through which a guide wire may be inserted through the catheter for purposes of guiding the catheter to the surgical area.

At catheter tip 108, the four optical fibers which pass through the catheter are arranged symmetrically so that the beams 110 overlap to illuminate a larger area. Tip 108 also has a bole on the center thereof, through which guidewire 112 can protrude to direct the catheter to the proper location.

FIGS. 9 and 10 show detailed views of the illustrative four-fiber catheter tip. The four optical fibers 42 and the inner shaft 40 which holds the fibers, are held in a fiber holder 50 which is preferably formed from a radiopaque material such as stainless steel or platinum. Fiber bolder 50 is cylindrical and is provided with a central aperture, 54, which communicates with a lumen 34 of approximately the same size that passes through the center of the catheter body 104. Fiber holder 50 is provided with a plurality of longitudinally extending holes 56 which extend through the wall of holder 50 and receive, in a snug fit, the distal ends of the fiber cores 42. The distal face 58 of the combined fiber cores 42 and holder 50 is polished flat to butt flush against optically transparent cap 52.

Cap 52 is cylindrical and has the same outer diameter as catheter body 104 so that the two pieces define a smooth and continuous diameter. Cap 52 may be formed of a transparent substance such as pyrex glass or sapphire and has an enlarged bore 62 extending in from its proximal end. Bore 62 terminates at its end to form internal shoulder 60. A smaller diameter central aperture, 64, is formed in the distal end of cap 52 which aperture may have the same diameter as aperture 54 in fiber holder 50 and lumen 34 in catheter body 104 to provide a smooth and continuous lumen which opens at the distal tip of the catheter. However, the aperture 64 in tip 52 may also be somewhat narrower than aperture 54 and lumen 34 as long as sufficient clearance is provided to accommodate a guidewire without adversely interfering with fluid flow and pressure measurements.

Cap 52 is secured by an epoxy adhesive (placed on its inner surface 62) to the fiber holder 50 and also to the portion of the inner shaft 40 and fibers 42 which are disposed within the proximal end of the cap 52. The distal end of the catheter body 104 is heat shrunk around the inner shaft 40 and fibers 42 to provide a smooth transition from cap 52 to catheter body 104.

More complete construction details of a four-fiber catheter suitable for use with the illustrative embodiment are given in co-pending U.S. patent application entitled "Wire Guided Laser Catheter", filed on May 22, 1985 by Stephen J. Herman, Laurence A. Roth, Edward L. Sinofsky and Douglas W. Dickinson, Jr.

Figure 11:
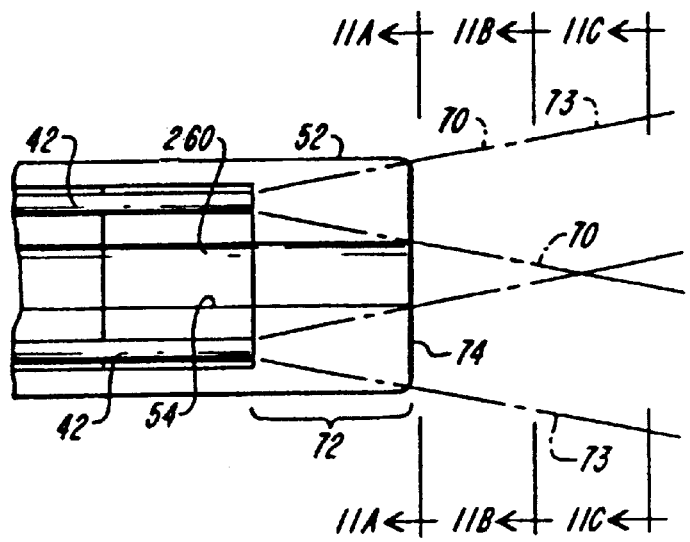
FIG. 11 is a side view of the probe tip of the catheter of FIG. 9.
Figure 11A:
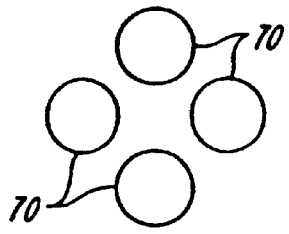
FIG. 11A is a schematic diagram of a beam pattern as viewed in the direction 11A–11A of FIG. 11.

FIG. 11 illustrates the output beam pattern developed by a four-fiber catheter, such as that described above, in which the four fibers are arranged in two diametrically-opposed pairs. The beam pattern from each of the four fiber ends is defined by a cone formed by the ray lines 70 in FIG. 11. The beam from each individual fiber 42 is emitted from the distal face of the fiber 42 and enters the distal segment 72 of cap 52 through the face defining the shoulder 60. The beam from each fiber is divergent and, in the illustrative embodiment, may have a half-angle in the range of 6°–16°, depending on the numerical aperture of the fibers which are used to construct the catheter.

Figure 11B:
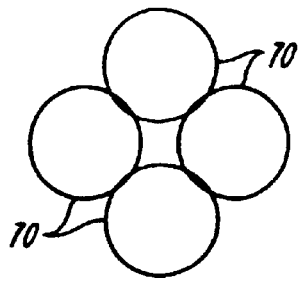
FIG. 11B is a schematic diagram of a beam pattern as viewed in the direction 11B–11B of FIG. 11.
Figure 11C:
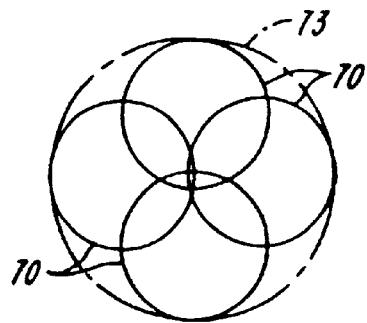
FIG. 11C is a schematic diagram of a beam pattern as viewed in the direction 11C–11C of FIG. 11.

The diverging beam from each of the fibers 42 exits from the distal emission face 74 at the end of cap 52. FIGS. 11, 11B and 11C illustrate the overall beam pattern (in cross-section) which is formed by the output of the four fibers as seen along image planes 11A, 11B and 11C in FIG. 11. At plane 11A, which is located at the emission face 74 of cap 52, the four beams in the illustrative embodiment are still separate. At plane 11B the diverging beams have spread further and have begun to overlap. At the plane indicated as 11C, the beams have overlapped and define an envelop 73 having an outer diameter which is slightly greater than the outer diameter of the catheter body 104. Preferably, at plane 11C, beams 70 will have overlapped to merge and cover a continuous pattern. Illustratively, such a merger will have occurred within a distance from the distal face 74 of tip 52 which is approximately equal to the outer diameter of catheter 104 (a typical diameter is 1.5 millimeters).

What is claimed is:

1. A surgical system comprising:
   a hollow elongate surgical instrument, having at least one lumen for receiving an optical fiber, and being maneuverable to provide a conduit for transmission of laser energy to a surgical site; and
   a flexible, elongate fiber for conducting laser energy from a proximal end of said fiber to a surgical site at a distal end of said fiber, the proximal end for receiving laser energy, and said fiber being a silica fiber including means for reducing absorption of laser energy at a wavelength of about 1.4–2.2 micrometers.

2. The system of claim 1, wherein said fiber is suitable for coupling with and conducting energy of a Holmium-doped Yttrium-Aluminum-Garnet laser.

3. The system of claim 1, wherein said fiber is suitable for coupling with and conducting energy of a Erbium-doped Yttrium-Aluminum-Garnet laser.

4. The system of claim 1, wherein said fiber is suitable for coupling with conducting energy from a Thulium-doped Yttrium-Aluminum-Garnet laser.

5. The system of claim 1, wherein said fiber is suitable for coupling with and conducting energy from a Holmium-doped Yttrium-Lithium-Fluoride laser.

6. The system of claim 1, wherein said fiber is suitable for coupling with and conducting energy from a Erbium-doped Yttrium-Lithium-Fluoride laser.

7. The system of claim 1, wherein the said fiber is suitable for conducting pulsed laser energy.

8. The system of claim 1, wherein the said fiber is suitable for conducting pulsed wave laser energy sufficient to remove biological tissue by vaporization.

9. The system of claim 1, wherein said fiber is suitable for conducting laser energy with a pulse width of 0.2–5 milliseconds.

10. The system of claim 1, wherein said fiber is suitable for conducting pulsed laser energy at a repetition rate of about 1 to about 10 pulses per second.

11. The system of claim 1, wherein said fiber is suitable for delivery of energy to a surgical site of at least 0.57 millijoules per pulse.

12. The system of claim 1 wherein the hollow elongate instrument is a catheter.

13. The system of claim 1 wherein the fiber is suitable for conducting continuous wave radiation.

14. The system of claim 13 wherein the fiber is suitable for to photocoagulate tissue.

* * * * *

Disclaimer

6,547,780 B1 — Edward Lawrence Sinofsky, Reading, MA (US). INFRARED LASER CATHETER SYSTEM. Patent dated Apr. 15, 2003. Disclaimer filed Sep. 14, 2009, by the assignee, CardioFocus, Inc.

Hereby disclaims claims 1, 3 and 6-14 of the patent.

*(Official Gazette, January 26, 2010)*

(12) EX PARTE REEXAMINATION CERTIFICATE (7547th)
United States Patent
Sinofsky

(10) Number: US 6,547,780 C1
(45) Certificate Issued: Jun. 1, 2010

(54) INFRARED LASER CATHETER SYSTEM

(75) Inventor: Edward Lawrence Sinofsky, Reading, MA (US)

(73) Assignee: CardioFocus, Inc

Reexamination Request:
No. 90/010,177, May 22, 2008
No. 90/009,185, Jun. 13, 2008
No. 90/010,198, Jun. 16, 2008

Reexamination Certificate for:
Patent No.: 6,547,780
Issued: Apr. 15, 2003
Appl. No.: 09/201,072
Filed: Nov. 30, 1998

Disclaimer of Claims 1, 3, 6, 7, 8, 9, 10, 11, 12, 13 and 14 Filed Sep. 14, 2009 (Jan. 26, 2010 O.G.).

Related U.S. Application Data

(63) Continuation of application No. 08/411,581, filed on Mar. 29, 1995, now Pat. No. 5,843,073, which is a continuation of application No. 08/049,147, filed on Apr. 19, 1993, now abandoned, which is a division of application No. 07/568,348, filed on Aug. 15, 1990, now Pat. No. 6,159,203, which is a continuation of application No. 07/257,760, filed on Oct. 14, 1988, now Pat. No. 4,950,266, which is a continuation of application No. 07/014,990, filed on Feb. 17, 1987, now abandoned, which is a continuation of application No. 06/761,188, filed on Jul. 31, 1985, now abandoned.

(51) Int. Cl.
*A61B 18/28* (2006.01)

(52) U.S. Cl. .................... 606/10; 606/3; 606/7; 606/13
(58) Field of Classification Search .................... None
See application file for complete search history.

(56) References Cited

U.S. PATENT DOCUMENTS

| | | | |
|---|---|---|---|
| 3,821,510 A | 6/1974 | Muncheryan | |
| 3,863,177 A | 1/1975 | Damen et al. | |
| 3,957,474 A | 5/1976 | Kobayashi et al. | |
| 4,037,113 A | 7/1977 | Moore | |
| 4,044,315 A | 8/1977 | Snitzer | |
| 4,114,980 A | 9/1978 | Asam et al. | |
| 4,164,373 A | 8/1979 | Schuss et al. | |
| 4,165,223 A | 8/1979 | Powers | |
| 4,165,915 A | 8/1979 | Rau et al. | |

(Continued)

FOREIGN PATENT DOCUMENTS

| | | |
|---|---|---|
| GB | 1535640 | 12/1978 |
| JP | S 56-73640 | 6/1981 |
| JP | S 57-17433 | 1/1982 |
| JP | S 57-34033 | 2/1982 |

OTHER PUBLICATIONS

Abela, George S. et al., Laser recanalization of occluded atherosclerotic arteries in vivo and in vitro, Laboratory Investigation Coronary Artery Disease, vol. 71, No. 2, pp. 403–411, Feb. 1985.

(Continued)

*Primary Examiner*—Cary E. O'Connor

(57) ABSTRACT

Laser energy produced by a laser operating In the mid-infrared region (approximately 2 micrometers) Is delivered by an optical fiber in a catheter to a surgical site for biological tissue removal and repair. Disclosed laser sources which have an output wavelength in this region include: Holmium-doped Yttrium Aluminum Garnet (Ho:YAG), Holmium-doped Yttrium Lithium Fluoride (Ho:YLF), Erbium-doped YAG, Erbium-doped YLF and Thulium-doped YAG. For tissue removal, the lasers are operated with relatively long pulses at energy levels of approximately 1 joule per pulse. For tissue repair, the lasers are operated in a continuous wave mode at low power. Laser output energy is applied to a silica-based optical fiber which has been specially purified to reduce the hydroxyl-ion concentration to a low level. The catheter may be comprised of a single optical fiber or a plurality of optical fibers arranged to give overlapping output patterns for large area coverage.

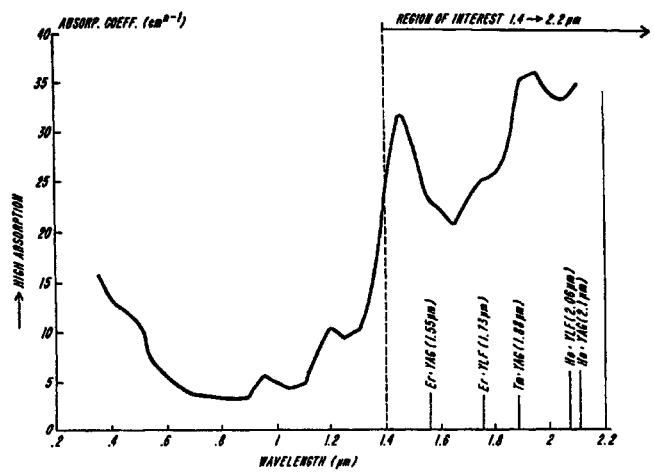

U.S. PATENT DOCUMENTS

| | | |
|---|---|---|
| 4,188,089 A | 2/1980 | Gliemeroth et al. |
| 4,206,968 A | 6/1980 | Suganuma et al. |
| 4,217,027 A | 8/1980 | MacChesney et al. |
| 4,225,330 A | 9/1980 | Kakuzen et al. |
| 4,235,615 A | 11/1980 | Rau et al. |
| 4,310,341 A | 1/1982 | Barns et al. |
| RE30,883 E | 3/1982 | Rau et al. .................. 65/60.51 |
| 4,321,559 A | 3/1982 | Esterowitz et al. |
| 4,389,230 A | 6/1983 | Modone et al. |
| 4,392,715 A | 7/1983 | Bonewitz et al. ......... 350/96.33 |
| 4,398,790 A | 8/1983 | Righini et al. |
| 4,406,516 A | 9/1983 | Hasegawa |
| 4,523,315 A | 6/1985 | Stone |
| 4,559,942 A * | 12/1985 | Eisenberg ...................... 606/6 |
| 4,560,246 A | 12/1985 | Cotter |
| 4,564,736 A | 1/1986 | Jones et al. |
| 4,567,366 A | 1/1986 | Shinohara |
| 4,800,876 A | 1/1989 | Fox et al. |
| 4,862,886 A * | 9/1989 | Clarke et al. .................. 606/7 |
| 5,009,655 A | 4/1991 | Daignault, Jr. et al. |
| 5,042,980 A | 8/1991 | Baker et al. |
| 5,071,417 A | 12/1991 | Sinofsky |
| 5,100,429 A | 3/1992 | Sinofsky et al. |
| 5,123,421 A | 6/1992 | Sinofsky |
| 5,135,001 A | 8/1992 | Sinofsky et al. |
| 5,207,669 A | 5/1993 | Baker et al. |
| 5,207,670 A | 5/1993 | Sinofsky |
| 5,254,112 A | 10/1993 | Sinofsky et al. |
| 5,261,904 A | 11/1993 | Baker et al. |
| 5,363,387 A | 11/1994 | Sinofsky |
| 5,540,677 A | 7/1996 | Sinofsky |
| 5,569,239 A | 10/1996 | Sinofsky |
| 5,632,767 A | 5/1997 | Sinofsky |
| 5,637,877 A | 6/1997 | Sinofsky |
| 5,643,253 A | 7/1997 | Baxter et al. |
| 5,725,522 A | 3/1998 | Sinofsky |
| 5,773,835 A | 6/1998 | Sinofsky |

OTHER PUBLICATIONS

DeShazer, Larry G., Advances in Infrared Fibers II, SPIE—The International Society for Optical Engineering, vol. 320, Jan. 26–28, 1982.

Ainslie, B.J., et al., Water Impurity in Low–Loss Silica Fibre, Mat. Res. Bull. vol. 12, pp. 481–488, 1977.

Stone, J. et al., Overtone Absorption and Raman Spectra of $H_2$ and $D_2$ in Silica Optical Fibers, AT&T Bell Laboratories Technical Journal, vol. 63, No. 6, Jul.–Aug. 1984.

Beales, K.J. et al., Increased Attenuation in Optical Fibres Caused by Diffusion of Molecular Hydrogen at Room Temperature, Electronics Letters, vol. 19, No. 20, pp. 917–919, Sep. 29, 1983.

Beck, R. et al., Ho laser with 50–W output and 6.5% slope efficiency, Journal of Applied Physics, vol. 46, No. 12, pp. 5224–5225, Dec. 1975.

Beck, W. B. et al., Hard Clad Silica: A New Family of Optical Fibers, Laser Focus, vol. 26, pp. 90–96, Dec. 1984.

Beckman, Hugh et al., Limbectomies, Keratectomies, and Keratostomies Performed with a Rapid–Pulsed Carbon Dioxide Laser, American Journal of Opthalmology, vol. 71, No. 6, pp. 1277–1283, Jun. 1971.

Brenci, M. et al., Quartz–plastic fibre technology and applications, Optica Acta, vol. 27, No. 8, pp. 1127–1141, 1980.

Brenci M. et al., Variable section optical–fiber delivery system of high power laser radiation for surgical use, Applied Optics, vol. 22, No. 3, pp. 373–375, Feb. 1, 1983.

Crowne, Douglas P., Selective Photothermolysis: Precise Microsurgery by Selective Absorption of Pulsed Radiation, Science, vol. 220, pp. 524–530, Apr. 29, 1983.

Excerpt from Optical Fiber Communication, Topical Meeting on Optical Fiber Communication, Mar. 6–8, 1979, pp. 38–41.

Itinerary for Colloquium on Implementation and Reliability of Optical Fibre Cable Links, Day 11, Electronics Division, Jun. 12, 1984.

European Conference on Optical Communication, Sep. 21–24, 1982.

Friebele, E. J. et al., Radiation Response of Fiber Optic Waveguides, IEE Transactions on Nuclear Science, vol. NS–25, No. 6, pp. 1261–1266, Dec. 1978.

Friebele, E. J. et al., Radiation–induced Optical Absorption Spectra of Fiber Optic Waveguides in the 0.4–1.7µ Region, pp. 355–367.

Fuller, Terry A., Carbon dioxide laser fiber optics in endoscopy, SPIE vol. 357, Lasers in Medicine and Surgery pp. 11–14, 1982.

Goldman, Leon, Laser medical instrumentation Med Instrum. 10, pp. 125–129 1976.

Goldman, Leon et al., Treatment of Portwine Marks by an Argon Laser, J. Dermatol. Surg. 2:5, pp. 385–388, Nov. 1976.

Hiehle, John F. et al., Nd–YAG Laser Fusion of Human Atheromatous Plaque–Arterial Wall Separations in Vitro, The American Journal of Cardiology, vol. 56, pp. 953–957, Dec. 1, 1985.

Horiguchi, Masaharu et al., Transmission–Loss Characteristics of Low–OH–Content Optical Fibers, Review of the Electrical Communication Laboratories, vol. 27, No. 3–4, pp. 226–235, Mar.–Apr. 1979.

Horiguchi, M. et al., This Week's Citation Classic. No. 34, Aug. 23, 1982.

Horn, Gerald D. et al., A new "cool" lens capsulotomy laser, AM Intra–Ocular Implant Soc J—vol. 8, pp. 337–342, Fall 1982.

Nussbaumer, H., Improved Approach for the Computation of Multidimensional Cosine Transforms, IBM Technical Disclosure Bulletin, vol. 23, No. 10, pp. 4517–4521, Mar. 1981.

Jacobsen, A. et al., Absorption and Scattering Losses in Glasses and Fibers for Light Guidance, pp. 187–188, 1971.

France, P.W. et al., OH–Absorption in Fluoride Glass Infra–red Fibres, Electronics Letters, vol. 20, No. 14, Jul. 5, 1984.

Karbe, E. et al., Experimental Liver and Kidney Surgery with CO2, CO, Holmium, and Neodym Lasers, Experimental Laser Surgery Study, 351, 179–192 (1980).

Itinerary for Lasers in Medicine, Proceedings of SPIE—The International Society for Optical Engineering, vol. 712, Sep. 15–17, 1986.

Marshall, A. et al., Hydrogen and Deuterium Gas–in–glass Effects in Single Mode Optical Fibres, Standard Telecommunication Laboratories Limited, 1984.

Brochure of Low Loss, Low Temperature Fiber Optic Cable, KSC 200 Series, Maxlight Fiber Optic Division, 1981.

Mirhoseini, M., Laser applications in thoracic and cardiovascular surgery, Journal of the Association for the Advancement of Medical Instrumentation, vol. 17, No. 9, pp. 401–403, Nov.–Dec. 1983.

Miya, T. et al., Ultimate Low–Loss Single–mode Fibre at 1.55μm, Electronic Letters, vol. 15, No. 4, pp. 106–108, Feb. 15, 1979.

Mochizuki, Kiyohumi et al., Behavoir of Hydrogen Molecules Adsorbed on Silica in Optical Fibers, IEEE Journal of Quantum Electronics, vol. QE–20, No. 7, pp. 694–697, Jul. 1984.

Moriyama, T. et al., Fabrication of Ultra–Low–OH Content Optical Fibers With VAD Method, pp. 18–21, 1980.

Mühlbauer, W. et al., Lichtbehandlung capillarer Jamangiome und Naevi flammei, Langenbecks Archiv fur Chirugie Supplement 1976.

Nakazawa, Masataka et al., 130–km–long fault location for single–mode optical fiber using 1.55–μm Q–switched $ER^{3+}$:glass laser, Optics Letter, vol. 9, No. 7, pp. 312–314, Jul. 1984.

Newman, D.H. et al., Sources for optical fibre communications, Telecommunications Journal vol. 48, pp. 673–680, 1981.

Volkov, V.V. et al., The User of Ytterbium–Erbium Laser in Clinical Opthalmology, pp. 3–6, 1983.

Annual Conference on Nuclear and Space Radiation Effects, IEEE transactions on Nuclear Science, vol. NS–25, No. 6, Dec. 1978.

Payne, D.N. et al., Preparation of Water–free Silica–based Optical–fibre Waveguide, Electronics Letters, vol. 10, No. 16, pp. 335–336, Aug. 8, 1974.

Quartz Products Corporation, brochure, "GSF series, low–loss, large diameter, silica cores" including price list dated Sep. 1979.

Quentel, G. et al., Laser Infrarouge Miniaturise Polyvalent, Bull. Soc. Opht. France, pp. 1249–1250, 1983.

Realization of Optical Fiber Extremity by NTT, Laser, pp. 28–29, 1981.

Rigterink, Merle D., Material Systems, Fabrication and Characteristics of Glass Fiber Optical Waveguides, Ceramic Bulletin, vol. 55, No. 9, pp. 775–780, 1976.

Russo, Vera et al., Lens–ended fibers for medical applications: a new fabrication technique, Applied Optics, vol. 23, No. 19, pp. 3277–3283, Oct. 1, 1984.

Russo, Vera, Fibers in Medicine I, New Directions in Guided Wave and Coherent Optics, vol. 1, pp. 247–270, 1984.

Sakaguchi, S. et al., Drawings–induced 1.53–μm wavelength optical loss in single–mode fibers drawn at high speeds, Appl. Phys. Lett., vol. 47, No. 4 pp. 344–345, Aug. 1985.

Shibata, Noriyoshi et al., Optical–Loss Characteristics of high $GeO_2$ Content Silica Fibers, The Transactions of the IECE of Japan, vol. E 63, No. 12, pp. 837–841, Dec. 1980.

Short Communication, Loss factors in optical fibres, Optical and Quantum Electronics, 13, pp. 85–89, 1981.

Itinerary for Sixth European Conference on Optical Communication, Sep. 16–19, 1980.

Tanaka, S. et al., Ultra–low–loss Single–Mode Fiber with Double Synthetic Cladding Layers, Quantum Electronics, IEEE Journal of vol. 17, Issue 6, pp. 835–849, Jun. 1981.

Tekaheshi, H. et al., $GeO_2$–$Sb_2O_3$ glass optical fibers for 2 to 3 m fabricated by vapor–phase axial deposition (VAD) method; SPIE vol. 320, Advances in Infrared Fibers II, pp. 88–92, 1982.

Derwent, Selection of Searches performed in Dialog databases, including, among others, "moriyama t," "VAD," "OH()Content," "vapor()phase()axial," and "flame()hydrolysis," produced by Lumenis in connection with *Cardio-Focus, Inc. v. Lumenis Inc.,* D. Mass., Civ. Case No. 06–CV–11242, 2006–2007.

Devore, D.P.; "Development and Applications of 2.1–μm Holmium Lasers", IEEE Journal of Quantum Electronics, vol. 9, Issue 6, Jun. 1973, pp. 664–665.

Kuhns, James G., et al.; Laser Injury in Skin, Laboratory Investigation, vol. 17, No. 1, Jul. 1967, pp. 1–13.

Beck et al., "Ho laser with 50–W output and 6.5% slope efficiency," Journal of Applied Physics, vol. 46, No. 12, Dec. 1975, pp. 5224–5225.

Stuck et al., "Ocular effects of holmium (2.08 ?m) and erbium (1.54 ?m) laser radiation," Health Physics, vol. 40, Jun. 1981, pp. 835–46.

Lin et al., "Tunable Fibre Raman Oscillator In The 1.32–1.41 μm Spectral Region Using A Low–Loss, Low OH–Single–Mode Fibre," Electronic Lettters, vol. 18, No. 16, Aug. 5, 1982, pp. 696–97.

Chida et al., "Fabrication of OH–free multimode fiber by vapor phase axial deposition" IEEE Journal of Quantum Electronics, vol. QE–18, No. 11, Nov. 1982, pp. 1883–1889 ("Chida").

Fuller, "Carbon dioxide laser fiber optics in endoscopy," Lasers in Medicine and Surgery, SPIE, vol. 357, 1982, pp. 11–14.

G. Lee et al., "The Current and Potential Uses of Lasers in the Treatment of Atherosclerotic Disease," Chest 85 pp. 429–434 (Mar. 1984).

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 2, 4 and 5 is confirmed.

Claims 1, 3 and 6-14 are now disclaimed.

\* \* \* \* \*

(12) EX PARTE REEXAMINATION CERTIFICATE (8487th)
United States Patent
Sinofsky

(10) Number: US 6,547,780 C2
(45) Certificate Issued: Aug. 23, 2011

(54) INFRARED LASER CATHETER SYSTEM

(75) Inventor: Edward Lawrence Sinofsky, Reading, MA (US)

(73) Assignee: Venture Lending & Leasing IV, Inc., San Jose, CA (US)

Reexamination Request:
No. 90/009,771, Jun. 30, 2010
No. 90/011,284, Oct. 15, 2010

Reexamination Certificate for:
Patent No.: 6,547,780
Issued: Apr. 15, 2003
Appl. No.: 09/201,072
Filed: Nov. 30, 1998

Reexamination Certificate C1 6,547,780 issued Jun. 1, 2010

Related U.S. Application Data

(63) Continuation of application No. 08/411,581, filed on Mar. 29, 1995, now Pat. No. 5,843,073, which is a continuation of application No. 08/049,147, filed on Apr. 19, 1993, now abandoned, which is a division of application No. 07/568,348, filed on Aug. 15, 1990, now Pat. No. 6,159,203, which is a continuation of application No. 07/257,760, filed on Oct. 14, 1988, now Pat. No. 4,950,266, which is a continuation of application No. 07/014,990, filed on Feb. 17, 1987, now abandoned, which is a continuation of application No. 06/761,188, filed on Jul. 31, 1985, now abandoned.

(51) Int. Cl.
*A61B 18/28* (2006.01)

(52) U.S. Cl. ............... 606/10; 606/3; 606/7; 606/13
(58) Field of Classification Search .................... None
See application file for complete search history.

(56) References Cited

U.S. PATENT DOCUMENTS

| | | | |
|---|---|---|---|
| 3,769,963 A | 11/1973 | Goldman et al. | |
| 3,821,510 A | 6/1974 | Muncheryan | |
| 3,858,577 A | 1/1975 | Bass et al. | |
| 3,863,177 A | 1/1975 | Damen et al. | |
| 3,865,113 A | 2/1975 | Sharon et al. | |
| 3,920,980 A | 11/1975 | Nath | |
| 3,957,474 A | 5/1976 | Kobayashi et al. | |
| 3,966,300 A | 6/1976 | Bernsee | |
| 4,037,113 A | 7/1977 | Moore | |

(Continued)

FOREIGN PATENT DOCUMENTS

| DE | 23 33 280 | 6/1973 |
|---|---|---|
| GB | 1535640 | 12/1978 |
| JP | S 56-73640 | 6/1981 |
| JP | S 57-17433 | 1/1982 |
| JP | S 57-34033 | 2/1982 |
| SU | 1073914 | 6/1985 |

OTHER PUBLICATIONS

Exhibit 3: Goodwin, Dr. D.W.; Lasers In Surgery; Physics & Technology; 1978; vol. 9, pp. 248–253; Great Britain
Exhibit 6: Heaney, et al; Transmittance and reflectance of crystalline quartz in high– and low–water content fused silica from 2 mm to 1 mm; Applied Optics, vol. 22. No. 24, Dec. 15, 1983, pp. 4069–4072.

(Continued)

*Primary Examiner* — Beverly M. Flanagan

(57) ABSTRACT

Laser energy produced by a laser operating In the mid-infrared region (approximately 2 micrometers) Is delivered by an optical fiber in a catheter to a surgical site for biological tissue removal and repair. Disclosed laser sources which have an output wavelength in this region include: Holmium-doped Yttrium Aluminum Garnet (Ho:YAG), Holmium-doped Yttrium Lithium Fluoride (Ho:YLF), Erbium-doped YAG, Erbium-doped YLF and Thulium-doped YAG. For tissue removal, the lasers are operated with relatively long pulses at energy levels of approximately 1 joule per pulse. For tissue repair, the lasers are operated in a continuous wave mode at low power. Laser output energy is applied to a silica-based optical fiber which has been specially purified to reduce the hydroxyl-ion concentration to a low level. The catheter may be comprised of a single optical fiber or a plurality of optical fibers arranged to give overlapping output patterns for large area coverage.

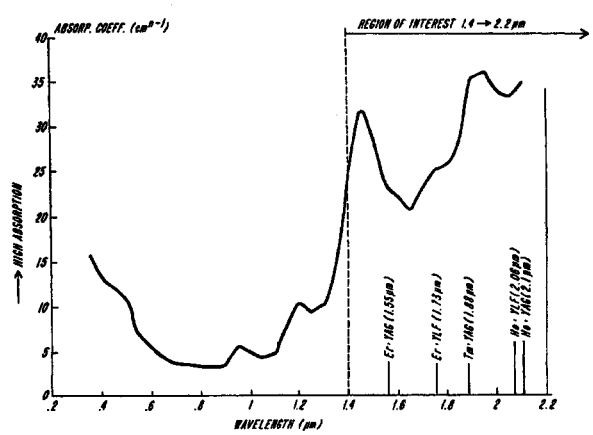

U.S. PATENT DOCUMENTS

| | | |
|---|---|---|
| 4,044,315 A | 8/1977 | Snitzer |
| 4,114,980 A | 9/1978 | Asam et al. |
| 4,164,373 A | 8/1979 | Schuss et al. |
| 4,165,223 A | 8/1979 | Powers |
| 4,165,915 A | 8/1979 | Rau et al. |
| 4,188,089 A | 2/1980 | Gliemeroth et al. |
| 4,217,027 A | 8/1980 | MacChesney et al. |
| 4,225,330 A | 9/1980 | Kakuzen et al. |
| 4,235,615 A | 11/1980 | Rau et al. |
| 4,310,341 A | 1/1982 | Baras et al. |
| 4,321,559 A | 3/1982 | Esterowitz et al. |
| 4,389,230 A | 6/1983 | Modone et al. |
| 4,392,715 A | 7/1983 | Bonewitz |
| 4,398,790 A | 8/1983 | Righini et al. |
| 4,406,516 A | 9/1983 | Hasegawa |
| 4,448,188 A | 5/1984 | Loeb |
| 4,501,993 A | 2/1985 | Mueller et al. |
| 4,519,390 A | 5/1985 | Horne |
| 4,523,315 A | 6/1985 | Stone |
| 4,559,942 A | 12/1985 | Eisenberg |
| 4,560,246 A | 12/1985 | Cotter |
| 4,564,736 A | 1/1986 | Jones et al. |
| 4,567,366 A | 1/1986 | Shinohara |
| 4,587,972 A | 5/1986 | Morantte, Jr. |
| 4,592,353 A | 6/1986 | Daikuzono |
| 4,633,866 A | 1/1987 | Peyman et al. |
| 4,641,650 A | 2/1987 | Mok |
| 4,669,467 A | 6/1987 | Willett et al. |
| 4,672,969 A | 6/1987 | Dew |
| 4,681,104 A | 7/1987 | Edelman |
| 4,718,417 A | 1/1988 | Kittrell et al. |
| 4,765,330 A | 8/1988 | Bach |
| 4,800,876 A | 1/1989 | Fox et al. |
| 4,848,339 A | 7/1989 | Rink et al. |
| 4,860,743 A | 8/1989 | Abela |
| 4,862,886 A | 9/1989 | Clarke et al. |
| 4,913,142 A | 4/1990 | Kittrell et al. |
| 4,967,745 A | 11/1990 | Hayes et al. |
| 4,994,059 A | 2/1991 | Kosa et al. |
| 4,994,060 A | 2/1991 | Rink |
| 5,009,655 A | 4/1991 | Daignault, Jr. et al. |
| 5,042,980 A | 8/1991 | Baker et al. |
| 5,071,417 A | 12/1991 | Sinofsky |
| 5,100,429 A | 3/1992 | Sinofsky et al. |
| 5,123,421 A | 6/1992 | Sinofsky |
| 5,135,001 A | 8/1992 | Sinofsky et al. |
| 5,147,354 A | 9/1992 | Boutacoff et al. |
| 5,207,669 A | 5/1993 | Baker et al. |
| 5,207,670 A | 5/1993 | Sinofsky |
| 5,254,112 A | 10/1993 | Sinofsky et al. |
| 5,261,904 A | 11/1993 | Baker et al. |
| 5,363,387 A | 11/1994 | Sinofsky |
| 5,540,677 A | 7/1996 | Sinofsky |
| 5,569,239 A | 10/1996 | Sinofsky |
| 5,632,767 A | 5/1997 | Sinofsky |
| 5,637,877 A | 6/1997 | Sinofsky |
| 5,643,253 A | 7/1997 | Baxter et al. |
| 5,725,522 A | 3/1998 | Sinofsky |
| 5,773,835 A | 6/1998 | Sinofsky |
| 6,547,780 B1 | 4/2003 | Sinofsky |

OTHER PUBLICATIONS

Exhibit 6: Heaney, et al; Transmittance and reflectance of crystalline quartz in high– and low–water content fused silica from 2 mm to 1 mm: Applied Optics, vol. 22. No. 24, Dec. 15, 1983, pp. 4069–4072.

Abela, George S. et al., Laser recanalization of occluded atherosclerotic arteries in vivo and in vitro, Laboratory Investigation Coronary Artery Disease, vol. 71, No. 2, pp. 403–411, Feb. 1985.

DeShazer, Larry G., Advances in Infrared Fibers II, SPIE—The International Society for Optical Engineering, vol. 320, Jan. 26–28, 1982.

Ainslie, B.J. et al., Water Impurity in Low–Loss Silica Fibre, Mat. Res. Bull. vol. 12, pp. 481–488, 1977.

Stone, J. et al., Overtone Absorption and Raman Spectra of $H_2$ and $D_2$ in Silica Optical Fibers, AT&T Bell Laboratories Technical Journal, vol. 63, No. 6, Jul.–Aug. 1984.

Beales, K.J. et al., Increased Attenuation in Optical Fibres Caused by Diffusion of Molecular Hydrogen at Room Temperature at Room Temperature, Electronics Letters, vol. 19, No. 20, pp. 917–919, Sep. 29, 1983.

Beck, R. et al., Ho Laser with 50–W output and 6.5% slope efficiency, Journal of Applied Physics, vol. 46, No. 12, pp. 5224–5225, Dec. 1975.

Beck, W. B. et al., Hard Clad Silica: A New Family of Optical Fibers, Laser Focus, vol. 26, pp. 90–96, Dec. 1984.

Beckman, Hugh et al., Limbectomies, Keratectomies, and Keratostomies Performed with a Rapid–Pulsed Carbon Dioxide Laser, American Journal of Opthalmology, vol. 71, No. 6, pp. 1277–1283, Jun. 1971.

Brenci, M. et al., Quartz–plastic fibre technology and applications, Optica Acta, vol. 27, No. 8, pp. 1127–1141, 1980.

Brenci M. et al., Variable section optical–fiber delivery system of high power laser radiation for surgical use, Applied Optics, vol. 22, No. 3, pp. 373–375, Feb. 1, 1983.

Chida et al., "Fabrication of OH–free multimode fiber by vapor phase axial deposition" IEEE Journal of Quantum Electronics, vol. QE–18, No. 11, Nov. 1982, pp. 1883–1889 ("Chida").

Crowne, Douglas P., Selective Photothermolysis: Precise Microsurgery by Selective Absorption of Pulsed Radiation, Science, vol. 220, pp. 524–530, Apr. 29, 1983.

Clear Fused Quartz Fluosil Preforms For Optical Waveguides, Heraeus Amersil, Exhibit 16 Sinafsky, Jan. 4, 1983.

Devore, D.P.; "Development and Applications of 2.1 µm Holmium Lasers" IEEE Journal of Quantum Electronics, vol. 9, Issue 6, Jun. 1973, pp. 664–665.

Excerpt from Optical Fiber Communication, Topical Meeting on Optical Fiber Communication, Mar. 6–8, 1979, pp. 38–41.

Itinerary for Colloquium on Implementation and Reliability of Optical Fibre Cable Links, Day 11, Electronics Division, Jun. 12, 1984.

European Conference on Optical Communication, Sep. 21–24, 1982.

Friebele, E. J. et al., Radiation Response of Fiber Optic Waveguides, IEE Transactions on Nuclear Science, vol. NS–25, No. 6, pp. 1261–1266, Dec. 1978.

Friebele, E. J. et al., Radiation–Induced Optical Absorption Spectra of Fiber Optic Waveguides in the 0.4–1.7µ Region, pp. 355–367.

Fuller, Terry A., Carbon dioxide laser fiber Optics in endoscopy, SPIE vol. 357, Lasers in Medicine and Surgery pp,. 11–14, 1982.

Goldman, Leon, Laser medical instrumentation Med Instrum. 10, pp. 125–129 1976.

Goldman, Leon et al., Treatment of Portwine Marks by an Argon Laser, J. Dermotol. Surg. 2:5, pp. 385–388, Nov. 1976.

Hale and Querry, "Optical constants of water in the 200 nm to 200 μm wavelength region," Applied Optics 12, 555 (1973).

Hiehle, John F. et al., Nd–YAG Laser Fusion of Human Atheromatous Plaque–Arterial Wall Separations in Vitro, The American Journal of Cardiology, vol. 56, pp. 953–957, Dec. 1, 1985.

Horiguchi, Masaharu et al., Transmission–Loss Characteristics of Low–OH–Content Optical Fibers, Review of the Electrical Communication Laboratories, vol. 27, No. 3–4, pp. 226–235, Mar.–Apr. 1979.

Horiguchi, M. et al., This Week's Citation Classic. No. 34, Aug. 23, 1982.

Horn, Gerald D. et al., A new "cool" lens capsulotomy laser, AM Intra–Ocular Implant Soc J—vol. 8, pp. 337–342, Fall 1982.

Nussbaumer, H., Improved Approach for the Computation of Multidimensional Cosine Transforms, IBM Technical Disclosure Bulletin, vol. 23, No. 10, pp. 4517–4521, Mar. 1981.

Jacobsen, A. et al., Absorption and Scattering Losses in Glasses and Fibers for Light Guidance, , pp. 187–188, 1971.

France, P.W. et al., OH–Absorption in Fluoride Glass Infra–red Fibres, Electronics Letters, vol. 20, No. 14, Jul. 5, 1984.

Karbe, E. et al., Experimental Liver and Kidney Surgery with CO2, CO, Holmium, and Neodym Lasers, Experimental Laser Surgery Study, 351, 179–192 (1980).

Kuhns et al., "Laser Injury in Skin," International Academy of Pathology 17, pp. 1–13 (1967).

Itinerary for Lasers in Medicine, Proceedings of SPIE—The International Society for Optical Engineering, vol. 712, Sep. 15–17, 1986.

Lin et al., "Tunable Fibre Raman Oscillator In The 1.32–1.41 μm Spectral Regional Using A Low–Loss, Low OH–Single–Mode Fibre," Electronics Letters, vol. 18, No. 16, Aug. 5, 1982, pp. 696–697.

Marshall, A. et al., Hydrogen and Deuterium Gas–in–glass Effects in Single Mode Optical Fibres, Standard Telecommunication Laboratories Limited, 1984.

Brochure of Low Loss, Low Temperature Fiber Optic Cable, KSC 200 Series, Maxlight Fiber Optic Division, 1981.

Mirhoseini, M., Laser applications in thoracic and cardiovascular surgery, Journal of the Association for the Advancement of Medical Instrumentation, vol. 17, No. 9, pp. 401–403, Nov.–Dec. 1983.

Miya, T. et al., Ultimate Low–Loss Single–mode Fibre at 1.55μm, Electronic Letters, vol. 15, No. 4, pp. 106–108, Feb. 15, 1979.

Mochizuki, Kiyohumi et al., Behavior of Hydrogen Molecules Adsorbed on Silica in Optical Fibers, IEEE Journal of Quantum Electronics, vol. QE–20, No. 7, pp. 694–697, Jul. 1984.

Moriyama, T. et al., Fabrication of Ultra–Low–OH Content Optical Fibers With VAD Method, pp. 18–21, 1980.

Mühlbauer, W. et al., Lichtbehandlung capillarer Jamangione und Naevi flammei, Langenbecks Archiv fur Chirugie Supplement 1976.

Nakazawa, Masataka et al., 130–km–long fault location for single–mode optical fiber using 1.55–μm Q–switched $ER^{3+}$:glass laser, Optics Letter, vol. 9, No. 7, pp. 312–314, Jul. 1984.

Newman, D.H. et al., Sources for optical fibre communications, Telecommunications Journal vol. 48, pp. 673–680, 1981.

Volkov, V.V. et al., The Use of Ytterbium–Erbium Laser in Clinical Opthalmology, pp. 3–6, 1983.

Annual Conference on Nuclear and Space Radiation Effects, IEEE transactions on Nuclear Science, vol. NS–25, No. 6, Dec. 1978.

Payne, D.N. et al., Preparation of Water–free Silica–based Optical–fibre Waveguide, Electronics Letters, vol. 10, No. 16, pp. 335–336, Aug. 8, 1974.

Quartz Products Corporation, brochure, "GSF series, low–loss, large diameter, silica cores" including price list dated Sep. 1979.

Quentel, G. et al., Laser Infrarouge Miniaturise Polyvalent, Bull. Soc. Opht. France, pp. 1249–1250, 1983.

Realization of Optical Fiber Extremity by NTT, Laser, pp. 28–29, 1981.

Rigterink, Merle D., Material Systems, Fabrication and Characteristics of Glass Fiber Optical Waveguides, Ceramic Bulletin, vol. 55, No. 9, pp. 775–780, 1976.

Russo, Vera et al., Lens–ended fibers for medical applications: a new fabrication technique, Applied Optics, vol. 23, No. 19, pp. 3277–3283, Oct. 1, 1984.

Russo, Vera, Fibers in Medicine I, New Directions in Guided Wave and Coherent Optics, vol. 1, pp. 247–270, 1984.

Sakaguchi, S. et al., Drawing–induced 1.53–μm wavelength optical loss in single–mode fibers drawn at high speeds, Appl. Phys. Lett., vol. 47, No. 4 pp. 344–345, Aug. 1985.

Shibata, Noriyoshi et al., Optical–Loss Characteristics of high $GeO_2$ Content Silica Fibers, The Transactions of the IECE of Japan, vol. E 63, No. 12, pp. 837–841, Dec. 1980.

Short Communication, Loss factors in optical fibres, Optical and Quantum Electronics 13, pp. 85–89, 1981.

Stuck et al., "Ocular effects of holmium (2.06 μm) and erbium (1.54 μm) laser radiation," Health Physics, vol. 40, Jun. 1981, pp. 835–846.

Itinerary for Sixth European Conference on Optical Communication, Sep. 16–19, 1980.

Tanaka, S. et al., Ultra–low–loss Single–Mode Fiber with Double Synthetic Cladding Layers, Quantum Electronics, IEEE Journal of vol. 17, Issue 6, pp. 835–849, Jun. 1981.

Tekaheshi, H. et al., $GeO_2$–$Sb_2O_3$ glass optical fibers for 2 to 3 m fabricated by vapor–phase axial deposition (VAD) method; SPIE vol. 320 Advances in Infrared Fibers II, pp. 88–92, 1982.

Derwent, Selection of Searches performed in Dialog databases, including, among others, "moriyama t," "VAD," "OH()Content," "vapor()phase()axial," and "flame()hydrolysis," produced by Lumenis in connection with *CardioFocus, Inc. v. Lumenis Inc.*, D. Mass., Civ. Case No. 06–CV–11242, 2006–2007.

Bruckner; "Properties and structure of vitrious silica" 1970 Journal of Non–crystaline Solids, vol. 5, pp. 123–175.

Beck et al., "HO lazer with 50-W output in 6.5% slope efficiency," Dec. 1975, Journal of Applied Physics, vol. 46, No. 12.

Karbe et al., "Experimental liver and kidney surgery with CO2, CO, Holmium, and Neodym lazers," 1980 Langerbecks Archiv fur Chirurgie, 351, 179–192 with English translation.

English translation of German Patent DE 23 33 280 A1, issued Jun. 29, 1973 to Gunther Nath.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 2 is confirmed.

Claims 1, 3 and 6-14 were previously disclaimed.

Claims 4 and 5 were not reexamined.

\* \* \* \* \*